(12) United States Patent
Toth

(10) Patent No.: US 6,280,084 B1
(45) Date of Patent: Aug. 28, 2001

(54) METHODS AND APPARATUS FOR INDIRECT HIGH VOLTAGE VERIFICATION IN AN IMAGING SYSTEM

(75) Inventor: Thomas L. Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/140,104

(22) Filed: Aug. 25, 1998

(51) Int. Cl.[7] .................................................. G01D 18/00
(52) U.S. Cl. ........................ 378/207; 378/207; 378/158; 378/159
(58) Field of Search .................................. 378/207, 111, 378/112, 158, 4, 159

(56) References Cited

U.S. PATENT DOCUMENTS

| | | | |
|---|---|---|---|
| 4,355,230 | * 10/1982 | Wilson et al. | 250/252.1 |
| 4,400,821 | * 8/1983 | Aichinger et al. | 378/97 |
| 4,697,280 | * 9/1987 | Zarnstorff et al. | 378/207 |
| 5,400,387 | * 3/1995 | Gard et al. | 378/207 |
| 5,430,785 | * 7/1995 | Pfoh et al. | 378/19 |
| 5,530,735 | * 6/1996 | Gard et al. | 378/207 |
| 5,706,326 | * 1/1998 | Gard | 378/19 |
| 5,982,846 | * 11/1999 | Toth et al. | 378/19 |
| 6,081,576 | * 6/2000 | Schanen et al. | 378/19 |
| 6,091,797 | * 7/2000 | Xie et al. | 378/62 |

FOREIGN PATENT DOCUMENTS

00079113 * 3/2000 (JP).

* cited by examiner

*Primary Examiner*—Frank G. Font
*Assistant Examiner*—Delma R. Flores Ruiz
(74) *Attorney, Agent, or Firm*—Armstrong Teasdale LLP; Christian G. Cabou

(57) ABSTRACT

The present invention, in one form, is a system which, in one embodiment, utilizes a pre-patient filter to attenuate detector array signals to indirectly determine a voltage applied to an x-ray source. Specifically, in one embodiment, the pre-patient filter includes a plurality of attenuating portions. By radiating an x-ray beam from the x-ray source through the different attenuating portions of the filter, the signals intensities at a detector array are attenuated differently. Utilizing an attenuation reference for the filter and a ratio of the measured attenuated signal intensities, the voltage applied to the x-ray source may indirectly be determined.

24 Claims, 5 Drawing Sheets

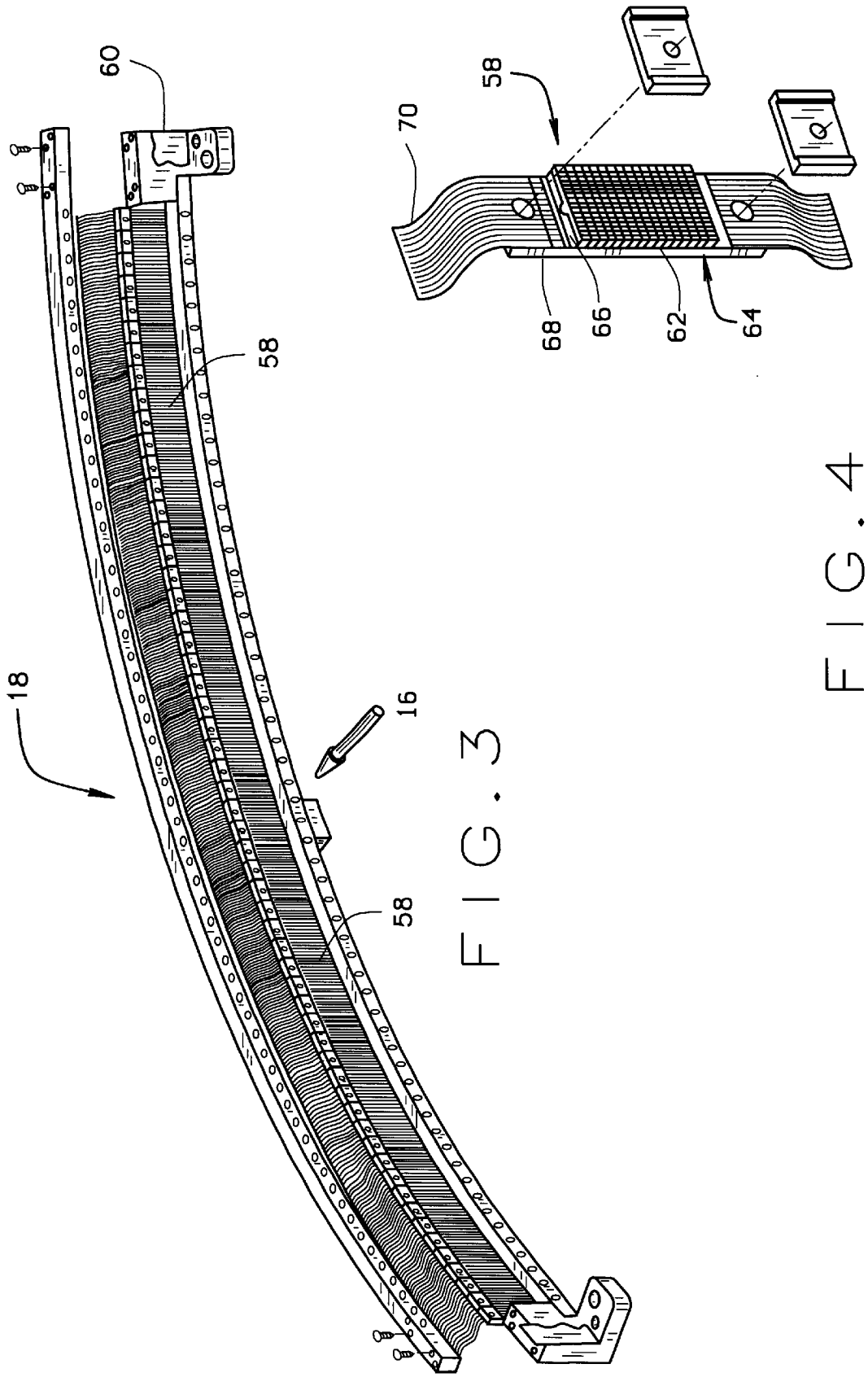

BODY BOWTIE ATTENUATION vs. FAN ANGLE (DEG.)

METHODS AND APPARATUS FOR INDIRECT HIGH VOLTAGE VERIFICATION IN AN IMAGING SYSTEM

BACKGROUND OF THE INVENTION

This invention relates generally to computed tomography (CT) imaging and more particularly, to measurement of x-ray source voltage in an imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Certain safety tests are typically required to be completed prior to delivering, after delivery, and when certain components are replaced. One such test is verification of the voltage applied to the x-ray source. This voltage is commonly called peak kilovolt (KVp) and the KVp is typically dependent on the type of imaging system and the x-ray source being used. Typical x-ray imaging systems are subject to errors and image artifacts caused by incorrect voltage (KVp) applied to the x-ray source. CT systems are particularly vulnerable to variations in source KVp, since CT systems rely on a known KVp to make corrections to the acquired data for effects such as beam hardening. The KVp stability of an imaging system may be degraded by such events as long-term component drift or component stress. As a result, KVp recalibration is performed regularly by service personnel and is very time consuming. In at least one known CT system separate commercial instruments are used to measure the KVp. These separate instruments typically require additional components to be added to the imaging system. These additional components create difficulty in obtaining repeatable results and increase the cost and complexity of the system. In addition, the additional components may require separate calibration and alignment procedures.

Accordingly, to obtain repeatable results of measuring KVp, it is desirable to provide an imaging system which determines the x-ray source voltage indirectly by utilizing a pre-patient filter and signal intensities from a detector array. It would also be desirable to provide such a system without increasing the cost and complexity of the system.

BRIEF SUMMARY OF THE INVENTION

These and other objects may be attained in a system which, in one embodiment, utilizes a pre-patient filter and intensity signals from a detector array to indirectly determine a voltage (KVp) applied to an x-ray source. More specifically and in one embodiment, the pre-patient filter is a bowtie filter and includes a plurality of attenuating portions.

In operation, by radiating the x-ray beam through the different attenuating portions of the filter, the signals intensities at the detector array are attenuated differently. In one embodiment, a scan is completed and intensity signals are measured for each cell of the detector array so that an intensity signal is generated for different attenuation portions of the filter. Utilizing an attenuation calibration reference for the different attenuation portions of the filter and a ratio of the measured attenuated signal intensities, the voltage applied to the x-ray source may indirectly be determined. The present invention is applicable to single slice and to multislice computed tomography systems, including two and four slice systems.

By utilizing the different attenuating portions of the pre-patient filter and detector array signal intensities, the x-ray source voltage is indirectly determined. In addition, the x-ray source voltage is determined without significantly increasing the cost or complexity of the system.

BRIEF DESCRIPTION OF THE DRAWINGS

FIG. 3 is a perspective view of a CT system detector array.

FIG. 4 is a perspective view of a detector module.

DETAILED DESCRIPTION OF THE INVENTION

Figure 1:
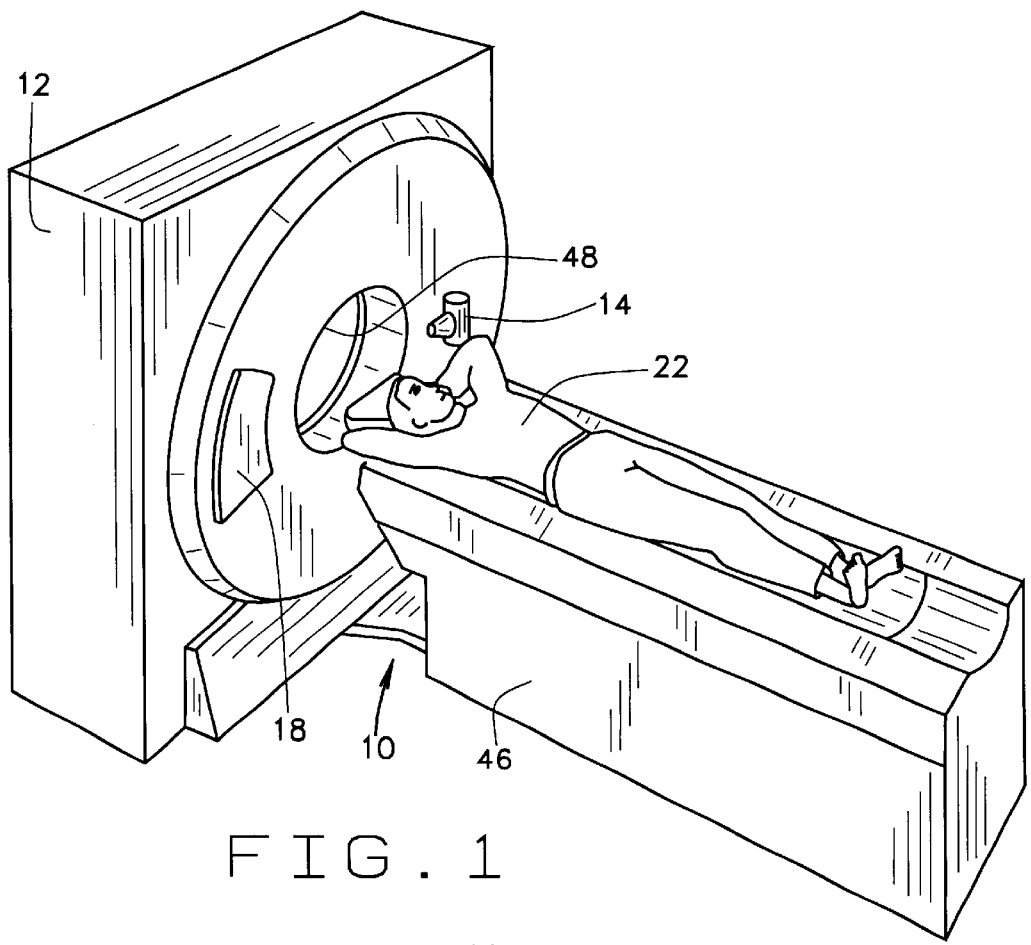
FIG. 1 is a pictorial view of a CT imaging system.
Figure 2:
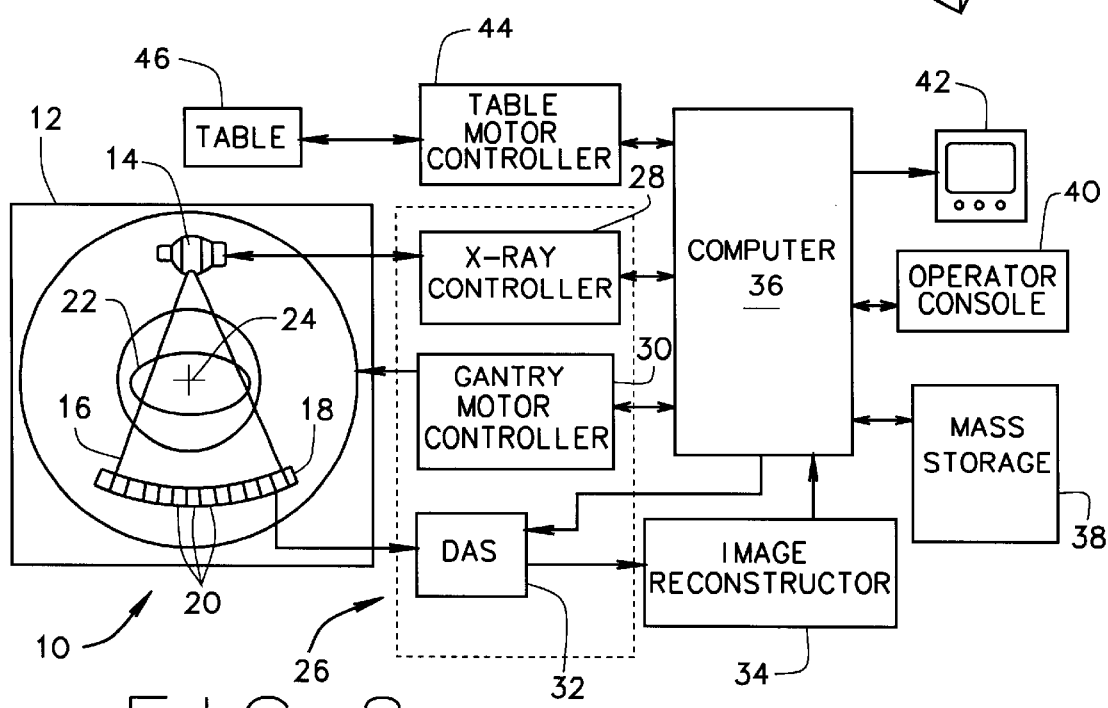
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements, or cells 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of the photodiode array are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
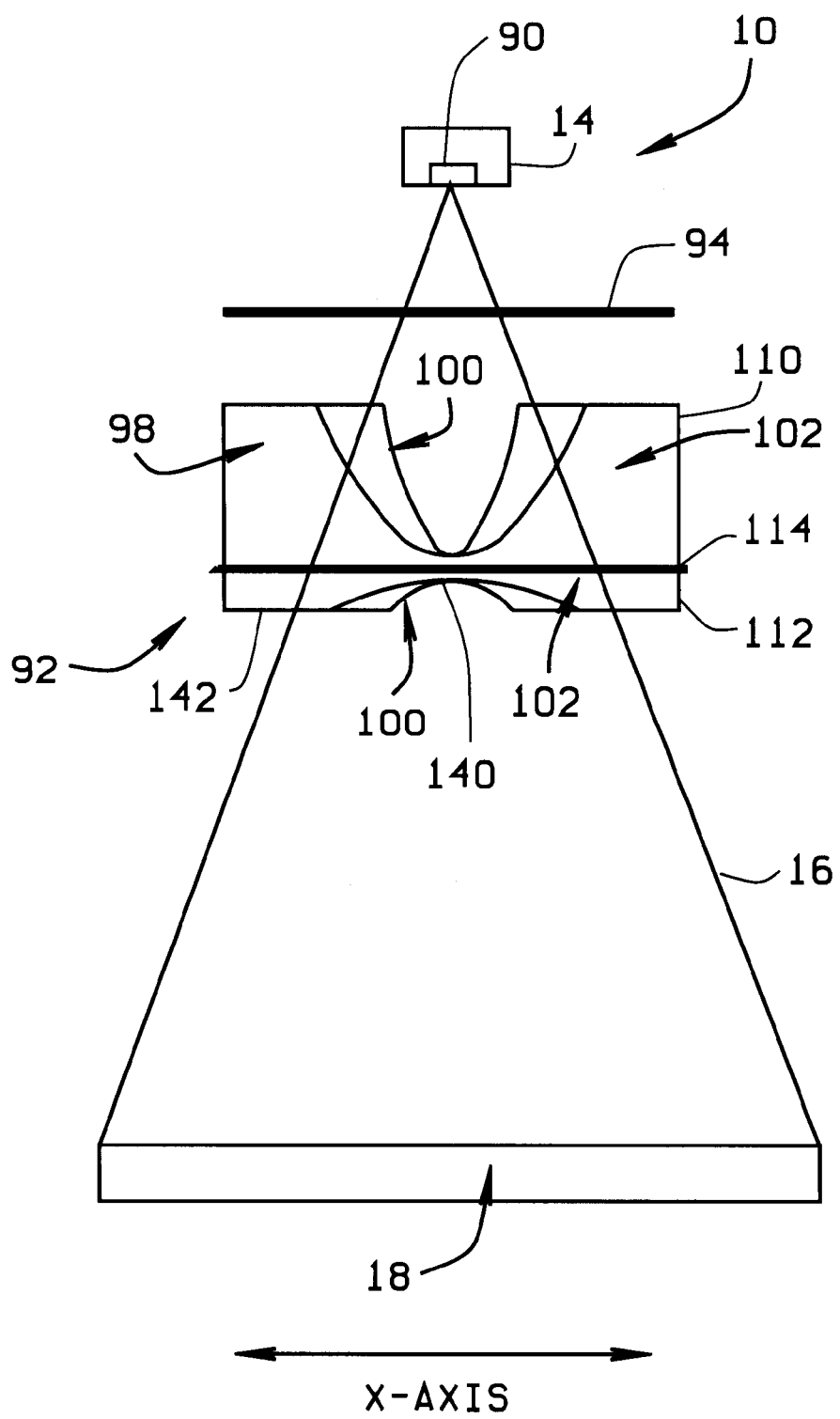
FIG. 5 is an x-axis schematic view of the CT imaging system shown in FIG. 1.
Figure 6:
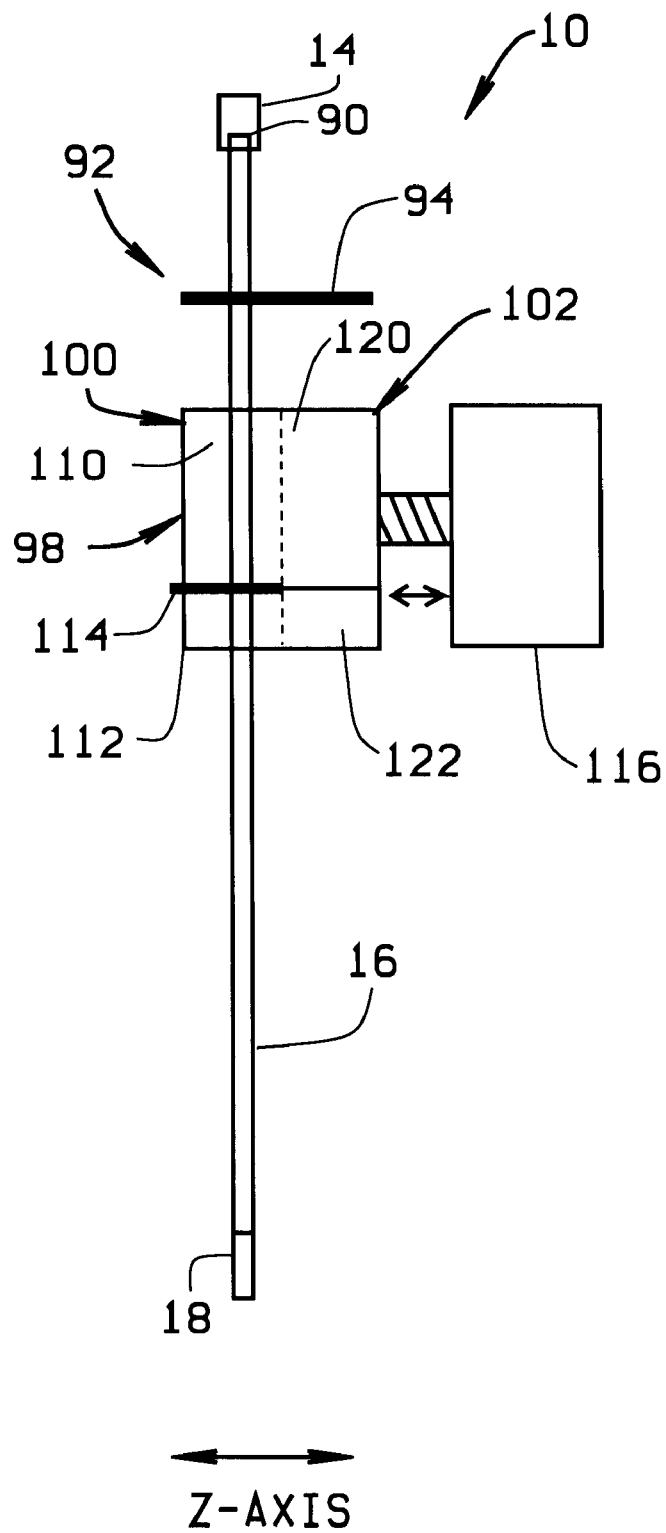
FIG. 6 is a z-axis schematic view of the CT imaging system shown in FIG. 5.

FIGS. 5 and 6 are schematic views of one embodiment of system 10 in accordance with the present invention. X-ray beam 16 emanates from a focal spot 90 of x-ray source 14. The intensity and quality of x-ray beam 16 is altered by filter assembly 92, and filtered beam 16 is projected toward detector array 18. More specifically and in one embodiment, filter assembly 92 includes a fixed filter portion 94, a z-axis movable filter 98 having a first filter 100 and a second filter 102. Respective filters 100 and 102 are configured to alter the intensity and quality of x-ray beam 16. More specifically, the shape and material composition of respective filters 100 and 102 are configured so that unique, or different, quality and intensity beams are created by filter assembly 92 based upon the position the movable filter 98. In one embodiment, depending on the z-axis position of filter assembly 92, beam 16 is filtered by first filter 100 or second filter 102.

Particularly and as shown in FIG. 6, first filter 100 includes a first filter material 110, a second filter material 112 and a third filter material 114 positioned between, or interposed, materials 110 and 112. In one embodiment, first filter 100 is configured as a bowtie filter and respective materials 110, 112, and 114 are graphite, aluminum, and copper. For example, material 110 may be 2.0 mm thick, material 112 may be 0.25 thick, and material 114 is about 75 micrometers thick so that first filter 100 is configured to generate a harder x-ray beam quality, for example to perform a body scan. In alternative embodiments, the number, thickness and shape of materials 110, 112, and 114 may selected to generate the desired, or selected attenuation characteristics.

Second filter 102, in one embodiment, includes a first filter material 120 and a second filter material 122. The physical configuration and selection for respective first and second filter materials 120 and 122 are selected so that an x-ray beam radiating from second filter 102 has an intensity and quality unique from an x-ray beam radiating from first filter 100. In one embodiment, second filter 102 is configured to generate a softer x-ray beam quality and the materials are selected from the same materials as respective materials 110 and 112, however the physical shape of second filter first and second materials 120 and 122 are altered. For example, second filter 102 is fabricated as a bowtie filter for generating a narrower x-ray beam and second portion first filter material 120 is graphite and second filter material 122 is aluminum. Utilizing the described second filter 102, a head scan can be performed. In alternative embodiments, respective shape and filter materials 120 and 122 may be selected from other shapes and materials other than materials 110 and 112. In addition, similar to filter 100, second filter 102 may include any number of materials.

More specifically, first filter 100 includes a first attenuation portion 140 and a second attenuation portion 142. As a result of the bowtie shape of filter 100, first attenuation portion 140 may be configured to be positioned at about a center of first filter 100 and second attenuation portion 142 may be positioned at an edge of filter 100. The amount of attenuation of respective portions 140 and 142 are determined by the thickness and attenuation characteristics of respective materials 110, 112 and 114. For example, at the center of first filter 100, the attenuation of portion 140 is, for example, a minimum attenuation value. Conversely, the amount of attenuation of portion 142 is, for example, a maximum attenuation value as a result of the physical characteristics of materials 110, 112 and 114.

In operation, filter assembly 92 is positioned so that x-ray beam 16 is radiated toward detector array 18. More specifically, movable filter 98 is positioned so that x-ray beam 16 is filtered using the appropriate filter of movable filter 92, for example first filter 100. A scan is then completed by filtering x-ray beam 16 with, for example, first filter 100, for a body scan. During the scan, signal intensities are collected, or measured, from detector array 18. Particularly, the signal intensity of each cell of detector array 18 is measured and the measured intensity signals represent the strength of x-ray beam 16 impinged upon detector array.

Figure 7:
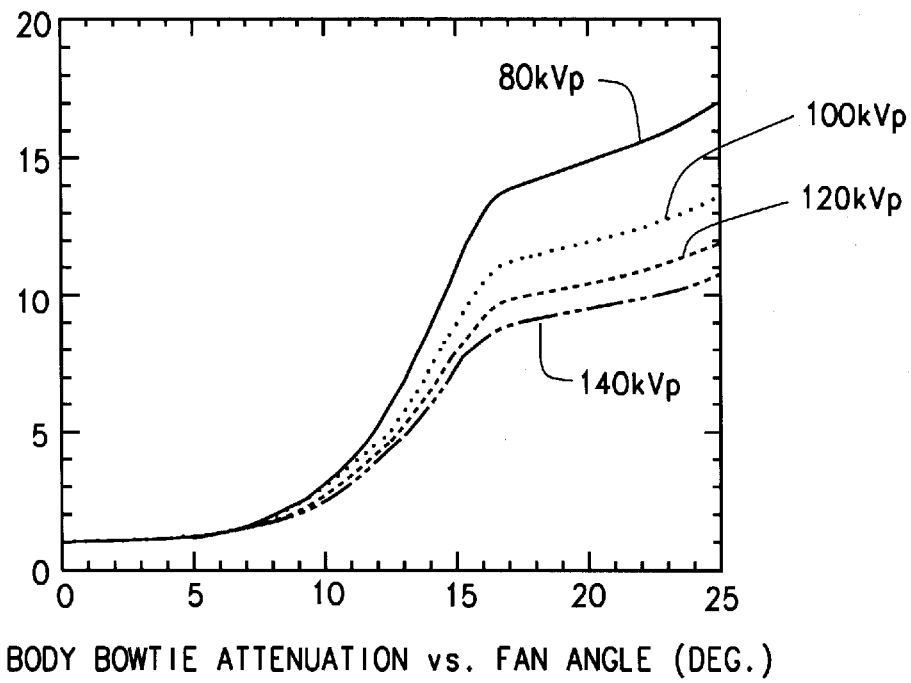
FIG. 7 is a graph illustrating filter attenuation versus fan angle.

In one embodiment, where the intensity signals are collected for a point in time, the intensity signal of each cell of detector array 18 represents the intensity for a corresponding fan angle of beam 16 and the attenuation portion of filter 92 for the specific angle. More specifically, for a detector cell located at an isocenter of detector array 18, the intensity signal represents a 0 degree fan angle. For a detector cell positioned away from the isocenter of detector array 18, for example at an end 150 of detector array 18, the intensity signal is representative of a second fan angle, for example 25 degrees. In one embodiment, for example, the intensity signal of the detector cell representative of the 0 degree fan angle is attenuated by first attenuation portion 140 of filter 100. The intensity signal simultaneously measured, or collected, from the detector cell representative of the 25 degree fan angle is attenuated by second attenuating portion 142 of filter 100. As a result, the intensity signal from a cell positioned near edge 150 of detector array 18 is attenuated more than the intensity signal from a cell positioned at the isocenter of detector array 18. For example and as shown in FIG. 7, attenuation of filter 100 is a function of fan angle and KVp.

Figure 8:
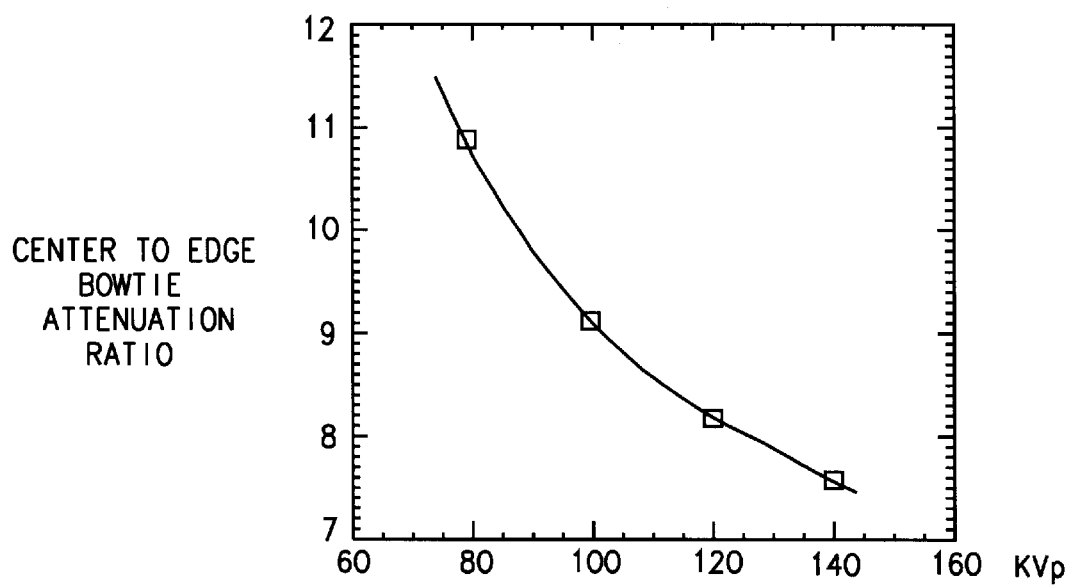
FIG. 8 is a graph illustrating filter center to edge attenuation ratio versus KVp.

The intensity signals from the isocenter of detector array 18 and the intensity signals from edge 150 of detector array 18 are then used to generate a measured center to edge bowtie attenuation ratio. Using the measured attenuation ratio, the x-ray source voltage is determined. More specifically, and in one embodiment, the x-ray source voltage, KVp, is determined by converting the measured attenuation ratio to a KVp value using a calibration function. Particularly, the calibration function is determined, for example once during fabrication of system 10, by performing a scan using filter 98, for example, filter 100. Scan data collected by detector array 18 is then processed to determine a mean attenuation ratio for the attenuation portions of filter 98, for example, first portion 140 and second portion 142 at different fan angles for at least one x-ray source reference voltage, for example 100 Kv. In one embodiment, the results are plotted and the resulting curve is fit to a third order polynomial, for example as shown in FIG. 8 illustrating filter center to edge attenuation ratio versus KVp. The polynomial coefficients and attenuation ratio are then stored, for example in a memory (not shown) of computer 36. The contents of the memory represents a calibrated x-ray source Kv) versus attenuation reference.

If an indirect measurement of the x-ray source voltage is desired during operation of system 10, the intensity signals from detector array 18 are used to generate the measured attenuation ratio. The measured attenuation ratio is then converted to a x-ray source voltage using the stored calibration polynomial. In one embodiment, the x-ray source voltage is:

$$KVp = k_0 + R*k_1 + R^2*k_2 + R^3*k_3$$

where:
R=measured attenuation ratio,
$k_0$, $k_1$, $k_2$, and $k_3$ are coefficients from the calibration polynomial.

In an alternative embodiment, the measured attenuation ratio is determined from a mean isocenter attenuation value and a mean edge attenuation value. The mean isocenter attenuation value is determined by collecting intensity signals from a first group of detector cells, for example from 90 channels surrounding the isocenter of array 18. The intensity signals from the first group of detector cells are then combined, or summed and an average, or mean, isocenter attenuation value is determined. The mean edge attenuation value is determined by collecting intensity signals from a second group of detector array cells, for example cells 1–90 and 822–912. The intensity signals from the second group of detector cells are then combined, or summed and an average, or mean, edge attenuation value is determined. The ratio of the mean isocenter attenuation value and the mean edge attenuation value is then used to determine KVp as described above.

The above described system utilizes different attenuating portions of the pre-patient filter and the detector array signal intensities to indirectly determine the x-ray source voltage. In addition, the described system also produces repeatable results without significantly increasing the cost or complexity of the system.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, the systems described may be used with any multislice system. In addition, the voltage determination procedure described above may be implemented in an algorithm stored in computer 36 or in a separate host computer. Accordingly, the spirit and scope of the invention are to be limited only by the terms of the appended claims.

What is claimed is:

1. A method of x-ray source voltage verification in an imaging system, the imaging system including a detector array, an x-ray source for radiating an x-ray beam toward the detector array and a pre-patient filter having at least a first attenuating portion and a second attenuating portion, said method comprising:

identifying signal intensities at the detector array from the x-ray beam radiated through the filter first attenuation portion;

identifying signal intensities at the detector array from the x-ray beam radiated through the filter second attenuation portion; and determining an x-ray source voltage based on the first attenuation portion signal intensities and the second attenuation portion signal intensities.

2. A method in accordance with claim 1 wherein the filter is a bowtie filter, the bowtie filter first attenuation portion positioned in a center of the filter and the second attenuation portion positioned at an edge of the filter, and wherein identifying signal intensities at the detector array from the x-ray beam radiated through the filter first attenuation portion comprises radiating the x-ray beam through a center portion of the filter.

3. A method of x-ray source voltage verification in an imaging system, the imaging system including a detector array, an x-ray source for radiating an x-ray beam toward the detector array and a pre-patient bowtie filter having at least a first attenuation portion positioned in a center of the filter and a second attenuation portion positioned at an edge of the filter, said method comprising:

identifying signal intensities at the detector array from the x-ray beam radiated through the filter first attenuation portion through a center portion of the filter at about a zero degree fan angle;

identifying signal intensities at the detector array from the x-ray beam radiated through the filter second attenuation portion; and determining an x-ray source voltage based on the first attenuation portion signal intensities and the second attenuation portion signal intensities.

4. A method in accordance with claim 2 wherein the detector array includes a plurality of detector cells displaced along an x-axis having an isocenter, wherein identifying signal intensities at the detector array from the x-ray beam radiated through the filter first attenuation portion comprises collecting intensity signals from at least one detector cell positioned near the isocenter.

5. A method in accordance with claim 4 wherein collecting intensity signals from at least one detector cell positioned near the isocenter comprises:

collecting intensity signals from a plurality of detector cells positioned near the isocenter; and determining a mean intensity signal based on the plurality of detector cell intensity signals.

6. A method in accordance with claim 4 wherein identifying signal intensities at the detector array from the x-ray beam radiated through the filter second attenuation portion comprises radiating the x-ray beam through the edge of the filter.

7. A method of x-ray source voltage verification in an imaging system, the imaging system including a detector array having a plurality of detector cells displaced along an x-axis having an isocenter, an x-ray source for radiating an x-ray beam toward the detector array and a pre-patient bowtie filter having at least a first attenuation portion positioned in a center of the filter and a second attenuation portion positioned at an edge of the filter, said method comprising:

identifying signal intensities at the detector array from the x-ray beam radiated through the first attenuation portion through a center portion of the filter, including collecting intensity signals from at least one detector cell positioned near the isocenter;

identifying signal intensities at the detector array from the x-ray beam radiated through the filter second attenuation portion through the edge of the filter at about a non-zero degree fan angle; and determining an x-ray source voltage based on the first attenuation portion signal intensities and the second attenuation portion signal intensities.

8. A method of x-ray source voltage verification in an imaging system, the imaging system including a detector array, an x-ray source for radiating an x-ray beam toward the detector array and a pre-patient filter having at least a first attenuating portion and a second attenuating portion, said method comprising:

identifying signal intensities at the detector array from the x-ray beam radiated through the filter first attenuation portion;

identifying signal intensities at the detector array from the x-ray beam radiated through the filter second attenuation portion; and determining an x-ray source voltage based on the first attenuation portion signal intensities and the second attenuation portion signal intensities;

wherein determining an x-ray source voltage based on the first attenuation portion signal intensities and the second attenuation portion signal intensities comprises:

determining an attenuation ratio based on the first filter first attenuation portion and the filter second attenuation portion; and generating a filter attenuation function based on the attenuation ratio.

9. A system for determining an x-ray source voltage in an imaging system, the imaging system including a detector array, an x-ray source for radiating an x-ray beam toward the detector array and a pre-patient filter having at least a first attenuating portion and a second attenuating portion, said system configured to:

identify signal intensities at the detector array from the x-ray beam radiated through the filter first attenuation portion;

identify signal intensities at the detector array from the x-ray beam radiated through the filter second attenuation portion; and determine an x-ray source voltage based on the first attenuation portion signal intensities and the second attenuation portion signal intensities.

10. A system in accordance with claim 9 wherein the filter is a bowtie filter, the bowtie filter first attenuation portion positioned in a center of the filter and the second attenuation portion positioned at an edge of the filter, and wherein to identify signal intensities at the detector array from the x-ray beam radiated through the filter first attenuation portion, said system configured to radiate the x-ray beam through a center portion of the filter.

11. A system for determining an x-ray source voltage in an imaging system, the imaging system including a detector array, an x-ray source for radiating an x-ray beam toward the detector array and a pre-patient bowtie filter having at least a first attenuating portion positioned in a center of the filter and a second attenuating portion positioned at an edge of the filter, said system configured to:

identify signal intensities at the detector array from the x-ray beam radiated through a first attenuation portion through a center portion of the filter at about a zero degree fan angle;

identify signal intensities at the detector array from the x-ray beam radiated through the filter second attenuation portion; and determine an x-ray source voltage based on the first attenuation portion signal intensities and the second attenuation portion signal intensities.

12. A system in accordance with claim 10 wherein the detector array includes a plurality of detector cells displaced along an x-axis having an isocenter, wherein to identify signal intensities at the detector array from the x-ray beam radiated through the filter first attenuation portion, said system configured to collect intensity signals from at least one detector cell positioned near the isocenter.

13. A system in accordance with claim 12 wherein to collect intensity signals from at least one detector cell positioned near the isocenter, said system configured to:

collect intensity signals from a plurality of detector cells positioned near the isocenter; and determine a mean intensity signal based on the plurality of detector cell intensity signals.

14. A system in accordance with claim 12 wherein to identify signal intensities at the detector array from the x-ray beam radiated through the filter second attenuation portion, said system configured to radiate the x-ray beam through the edge of the filter.

15. A system for determining an x-ray source voltage in an imaging system, the imaging system including a detector array having a plurality of detectors cells displaced along an x-axis having an isocenter, an x-ray source for radiating an x-ray beam toward the detector array and a pre-patient bowtie filter having at least a first attenuating portion positioned in a center of the filter and a second attenuating portion positioned at an edge of the filter, said system configured to:

identifying signal intensities at the detector array from the x-ray beam radiated through the first attenuation portion through a center portion of the filter, including collecting intensity signals from at least one detector cell positioned near the isocenter;

identify signal intensities at the detector array from the x-ray beam radiated through the filter second attenuation portion through the edge of the filter at about a non-zero degree fan angle; and determine an x-ray source voltage based on the first attenuation portion signal intensities and the second attenuation portion signal intensities.

16. A system for determining an x-ray source voltage in an imaging system, the imaging system including a detector array, an x-ray source for radiating an x-ray beam toward the detector array and a pre-patient filter having at least a first attenuating portion and a second attenuating portion, said system configured to:

identify signal intensities at the detector array from the x-ray beam radiated through the filter first attenuation portion;

identify signal intensities at the detector array from the x-ray beam radiated through the filter second attenuation portion; and determine an x-ray source voltage based on the first attenuation portion signal intensities and the second attenuation portion signal intensities; and wherein to determine an x-ray source voltage based on the first attenuation portion signal intensities and the second attenuation portion signal intensities, said system configured to:

determine an attenuation ratio based on the filter first attenuation portion and the filter second attenuation portion; and generate a filter attenuation function based on the attenuation ratio.

17. An imaging system comprising a multislice detector array, an x-ray source for radiating an x-ray beam toward the detector array, a pre-patient filter having at least a first attenuating portion and a second attenuating portion and a computer, said computer coupled to said detector array and said x-ray source and programmed to:

identify signal intensities at said detector array from said x-ray beam radiated through said filter first attenuation portion;

identify signal intensities at said detector array from said x-ray beam radiated through said filter second attenuation portion; and determine an x-ray source voltage based on said first attenuation portion signal intensities and said second attenuation portion signal intensities.

18. A system in accordance with claim 17 wherein said filter is a bowtie filter, said bowtie filter first attenuation portion positioned in a center of said filter and said second attenuation portion positioned at an edge of said filter, and wherein to identify said signal intensities at said detector array from said x-ray beam radiated through said filter first attenuation portion, said computer programmed to radiate said x-ray beam through a center portion of said filter.

19. An imaging system comprising a multislice detector array, an x-ray source for radiating an x-ray beam toward the detector array, and a pre-patient bowtie filter having at least a first attenuating portion in a center of said filter and a second attenuating portion positioned at an edge of said filter and a computer, said computer coupled to said detector array and said x-ray source and programmed to:

identify signal intensities at said detector array from said x-ray beam radiated through said filter first attenuation portion through said filter center portion at about a zero degree fan angle;

identify signal intensities at said detector array from said x-ray beam radiated through said filter second attenuation portion; and determine an x-ray source voltage based on said first attenuation portion signal intensities and said second attenuation portion signal intensities.

20. A system in accordance with claim 18 wherein said detector array includes a plurality of detector cells displaced along an x-axis having an isocenter, wherein to identify said signal intensities at said detector array from the x-ray beam radiated through the filter first attenuation portion, said computer programmed to collect intensity signals from at least one detector cell positioned near said isocenter.

21. A system in accordance with claim 20 wherein to collect said intensity signals from at least one detector cell positioned near said isocenter, said computer programmed to:

collect said intensity signals from a plurality of detector cells positioned near said isocenter; and determine a mean intensity signal based on said plurality of detector cell intensity signals.

22. A system in accordance with claim 20 wherein to identify said signal intensities at said detector array from said x-ray beam radiated through said filter second attenuation portion, said computer programmed to radiate said x-ray beam through said edge of said filter.

23. An imaging system comprising a multislice detector array, an x-ray source for radiating an x-ray beam toward the detector array, a pre-patient bowtie filter having at least a first attenuating portion in a center of said filter and a second attenuating portion positioned at an edge of said filter and a computer, said computer coupled to said detector array and said x-ray source and programmed to:

identify signal intensities at said detector array from said x-ray beam radiated through said filter first attenuation portion through a center portion of said filter, including collecting intensity signals from at least one detector cell positioned near the isocenter;

identify signal intensities at said detector array from said x-ray beam radiated through said filter second attenuation portion through the edge of said filter at about a non-zero degree fan angle; and determine an x-ray source voltage based on said first attenuation portion signal intensities and said second attenuation portion signal intensities.

24. An imaging system comprising a multislice detector array, an x-ray source for radiating an x-ray beam toward the detector array, a pre-patient filter having at least a first attenuating portion and a second attenuating portion and a computer, said computer coupled to said detector array and said x-ray source and programmed to:

identify signal intensities at said detector array from said x-ray beam radiated through said filter first attenuation portion;

identify signal intensities at said detector array from said x-ray beam radiated through said filter second attenuation portion; and determine an x-ray source voltage based on said first attenuation portion signal intensities and said second attenuation portion signal intensities; and wherein to determine an x-ray source voltage based on said first attenuation portion signal intensities and said second attenuation portion signal intensities, said computer programmed to:

determine an attenuation ratio based on the filter first attenuation portion and the filter second attenuation portion; and generate a filter attenuation function based on the attenuation ratio.

* * * * *

UNITED STATES PATENT AND TRADEMARK OFFICE
CERTIFICATE OF CORRECTION

PATENT NO.         : 6,280,084 B1                                      Page 1 of 1
APPLICATION NO. : 09/140104
DATED              : August 28, 2001
INVENTOR(S)        : Thomas L. Toth It is certified that error appears in the above-identified patent and that said Letters Patent is hereby corrected as shown below:

Column 1, line 37, delete "that" and insert therefor -- the --.

Column 4, line 1, delete "disable" and insert therefor -- disabled --.

Column 4, line 45, delete "position the" and insert therefor -- position of the --.

Column 4, line 59, delete "may selected" and insert therefor -- may be selected --.

In Claim 15, column 9, line 44, delete "identifying" and insert therefor -- identify --.

Signed and Sealed this

Twenty-second Day of May, 2007

JON W. DUDAS
*Director of the United States Patent and Trademark Office*